United States Patent
Chambon

(10) Patent No.: US 8,736,282 B2
(45) Date of Patent: May 27, 2014

(54) DEVICE FOR THE CAPACITIVE MEASUREMENT OF THE QUALITY AND/OR DETERIORATION OF A FLUID

(75) Inventor: Gérald Chambon, Lausanne (CH)

(73) Assignee: Alpsens Technologies Inc., Ecublens (CH)

( * ) Notice: Subject to any disclaimer, the term of this patent is extended or adjusted under 35 U.S.C. 154(b) by 782 days.

(21) Appl. No.: 12/602,079

(22) PCT Filed: Apr. 18, 2008

(86) PCT No.: PCT/EP2008/054746
§ 371 (c)(1),
(2), (4) Date: Mar. 30, 2010

(87) PCT Pub. No.: WO2008/135368
PCT Pub. Date: Nov. 13, 2008

(65) Prior Publication Data
US 2011/0234244 A1    Sep. 29, 2011

(30) Foreign Application Priority Data

Apr. 20, 2007 (CH) ....................................... 0654/07

(51) Int. Cl.
*G01R 27/26* (2006.01)
*G01R 27/08* (2006.01)

(52) U.S. Cl.
USPC .......................................... 324/663; 324/698

(58) Field of Classification Search
USPC ................... 324/663, 686, 519, 698
See application file for complete search history.

(56) References Cited

U.S. PATENT DOCUMENTS

| | | | |
|---|---|---|---|
| 6,469,521 B1 | 10/2002 | Klun et al. | |
| 6,777,009 B1 | 8/2004 | Shealy | |
| 6,822,461 B2 | 11/2004 | Klun | |
| 7,504,836 B2 * | 3/2009 | Chambon et al. | 324/698 |
| 2006/0288877 A1 | 12/2006 | Chambon et al. | |

FOREIGN PATENT DOCUMENTS

| | | |
|---|---|---|
| EP | 1 393 664 | 3/2004 |
| EP | 1 588 158 B1 | 3/2007 |
| JP | 61-44339 | 3/1986 |
| WO | 2004/065957 A1 | 8/2004 |
| WO | 2005/098406 A1 | 10/2005 |

OTHER PUBLICATIONS

Testo, "Cooking Oil Tester with Display and Alarm," from http://www.appleonehk.com/265_E.pdf, Feb. 2004, pp. 1-2.

(Continued)

*Primary Examiner* — Amy He
(74) *Attorney, Agent, or Firm* — Griffin & Szipl, P.C.

(57) ABSTRACT

A device for capacitive measurement of the quality and/or deterioration of a fluid includes a sensor encapsulated in a perforated case fixed in the vat of a cooking apparatus that has a bottom, wherein the sensor is connected to an electronic processing circuit, wherein the sensor includes a pair of flat electrodes each having the shape of a comb with a plurality of teeth, which are approximately parallel to each other and extends from a base, wherein the electrodes are arranged relative to each other so teeth of one electrode fit between teeth of the other electrode in approximately the same plane, and the encapsulated sensor is oriented in the vat so the longitudinal axis of each electrode base extends parallel to the bottom of the vat and so the plane of the sensor electrodes forms an angle of between 0° and 60° with the vertical direction.

8 Claims, 4 Drawing Sheets

(56) References Cited

OTHER PUBLICATIONS

International Search Report issued in corresponding application No. PCT/EP2008/054746, completed Jul. 18, 2008 and mailed Jul. 29, 2008.

Office Action issued Jul. 18, 2012 in co-pending related U.S. Appl. No. 12/602,070.

http://www.thefreedictionary.com/p/axis (2013).

http://www.thefreedictionary.com/p/parallel (2013).

* cited by examiner

DEVICE FOR THE CAPACITIVE MEASUREMENT OF THE QUALITY AND/OR DETERIORATION OF A FLUID

This is a National Phase Application in the United States of International Patent Application No. PCT/EP2008/054746 filed Apr. 18, 2008, which claims priority on Swiss Patent Application No. 00654/07, filed Apr. 20, 2007. The entire disclosures of the above patent applications are hereby incorporated by reference.

FIELD OF THE INVENTION

The present invention concerns a device for the capacitive measurement of the quality and/or deterioration of a fluid, in particular an oil. The invention particularly concerns a device of this type that has a capacitive sensor for measuring the quality and/or deterioration of cooking oil, which is arranged directly in the cooking apparatus, and wherein the capacitive sensor is oriented such that it significantly improves the quality and reliability of the capacitive measurement.

BACKGROUND OF THE INVENTION

It is well know that edible oils deteriorate during cooking, particularly when they are repeatedly heated to high temperatures. These oils are typically heated to temperatures of the order of 180° C. to fry food. A multitude of chemical reactions occur at these temperatures, such as polymerisation, thermo-oxidation, etc., which significantly alter the quality of the oil. The quantity of some products of these reactions must not exceed a threshold imposed by legislation, since the oil is deemed unfit for consumption beyond the threshold. It is thus important to be able to detect the threshold in a reliable manner, so that the oil is replaced as soon as it becomes necessary. For a long time, it was left to cooks to judge, after a visual and/or olfactory inspection, whether the oil was still fit for consumption. Of course, that method is entirely subjective and is consequently unreliable.

EP Patent No, 1 588 158 discloses a device for the capacitive measurement of the quality and/or deterioration of a cooking oil to overcome these drawbacks. The content of EP Patent No, 1 588 158, as well as its U.S. equivalent, namely, U.S. Pat. No. 7,504,836 B2, are incorporated herein by reference. In this device, the capacitive sensor is directly arranged in the vat of the cooking apparatus, with the sensor encapsulated in a perforated protective case, secured in a submerged area of the vat.

Although the device disclosed in that patent application operates satisfactorily, performing a capacitance measurement inside a deep fat fryer remains a highly delicate operation.

During his research, the Applicant discovered that the position or orientation of the sensor inside the vat is crucial for obtaining a reliable capacitive measurement. Indeed, both water and impurities in the oil and temperature gradients present in the vat have a significant effect on the measurement and the accuracy thereof.

Water, mainly present in new oil and in food for frying, finds its place at the bottom of the vat when the oil temperature is less than 100° C. When the temperature of the oil rises, it creates a "hot" area above the heating element (approx. 180° C.) and possibly a "cold" area (approx. 80° C.) below the heating element if the deep fat fryer is provided for this purpose. The water generated by cooking may remain fractionated with the oil when its temperature is less than 100° C.

When food is being cooked, water is discharged because of the cooking chemistry. Part of the water passes from the liquid state to the steam state, which will produce natural mixing, which will also cause the water at the bottom of the vat to rise. The operator often performs mechanical stirring to cook the food better.

It is when drops of water or steam become blocked in the sensor or at the surface thereof, that the measured value becomes unusable.

Moreover, impurities, mainly formed of breadcrumbs and bits of cooked food, dirty the sensor, mainly on the sensitive surface thereof and over any closed part of the encapsulating case. These impurities thus also tend to damage the measurement quality.

The capacitive measurement is also greatly influenced by the temperature gradients present in the vat. When a deep fat fryer is switched on, the temperature above the heating element reaches approximately 180° C. Underneath the heating element, the temperature increases slowly if there is no mixing caused by the insertion of products for frying, which pushes the hot oil from the top to the bottom. Mixing the oil causes temperature differences on the sensitive surface of the sensor. This thermal gradient may be very marked and the temperature variations may be very rapid when products for frying are dipped into the vat.

The temperature greatly influences the dielectric constant of the oil, and thus its capacitance, which, in this case, decreases. Temperature measurement, and mainly the measuring point thereof, is thus also an essential element for the accuracy of the system.

SUMMARY OF THE INVENTION

It is thus an object of the invention to overcome this problem by providing a device for the capacitive measurement of the quality and/or deterioration of an oil that includes a sensor, encapsulated in a perforated case, secured in the vat of a cooking apparatus that includes a bottom, wherein the sensor is connected to an electronic processing circuit, and the sensor includes a pair of flat electrodes, which each have the shape of a comb with a plurality of teeth that are approximately parallel to each other and extend from a base, the electrodes are arranged relative to each other such that the teeth of one electrode fit between the teeth of the other electrode in approximately the same plane, characterized in that the encapsulated sensor is oriented in the vat such that the longitudinal axis of the base of each electrode extends parallel to the bottom of the vat and in that the plane of the sensor electrodes forms an angle of between 0° and 60° with the vertical direction.

According to one advantageous feature, the plane of the sensor electrodes forms an angle of between 0° and 30° with the vertical direction. According to a preferred feature, the plane of the sensor electrodes forms an angle of zero degrees with the vertical direction. According to another feature of the device, the sensor is secured in the vat in a removable manner on a securing support. According to yet another feature of the device, the sensor is directly secured underneath the heating element of the cooking apparatus.

The orientation of the encapsulated sensor minimises the effects of the temperature gradient: assuming that the oil is composed of isotherms (same depth in the vat=same temperature). The encapsulated sensor is placed "on its side" or edge in the deep fat fryer (narrow pointed side pointing upwards) to minimise the flat surfaces where breadcrumbs and water could accumulate.

The structure of the sensor and the encapsulating case thereof are open as far as possible, allowing the oil to flow naturally. This flow guarantees permanent "cleaning" of the sensor and eliminates accumulated dirt.

According to one embodiment, a temperature sensor is associated with the sensor, located on the sensor surface, with the sensitive part against the exterior. This position allows the temperature of the oil to be measured as close as possible to the sensor surface.

The encapsulated sensor is removable. It is thus possible to remove it from the vat to clean it in case the deep fat fryer preventative maintenance (cleaning, boil-out . . . ) is insufficient.

These features ensure that the sensor operates in an optimum manner and improve the capacitive measurement accuracy, simply and efficiently. One important advantage is that the main problems inherent in any fryer are avoided by well thought out positioning and suitable design during development and installation. Furthermore then, in accordance with a first non-limiting illustrative embodiment of the present invention, a device is provided for the capacitive measurement of the quality and/or deterioration of a fluid that includes a sensor encapsulated in a perforated case and secured in the vat of a cooking apparatus, which includes a bottom, wherein the sensor is connected to an electronic processing circuit, wherein the sensor includes a pair of flat electrodes that each have the shape of a comb with a plurality of teeth, which are approximately parallel to each other and extend from a base, wherein the electrodes are arranged in relation to each other such that the teeth of one electrode fit between the teeth of the other electrode in approximately the same plane, and wherein the encapsulated sensor is oriented in the vat such that the longitudinal axis of the base of each electrode extends parallel to the bottom of the vat and in that the plane of the sensor electrodes form an angle of between 0° and 60° with the vertical direction. In accordance with a second non-limiting, illustrative embodiment of the present invention, the first non-limiting embodiment is modified so that the plane of the sensor electrodes forms an angle of between 0° and 30° with the vertical direction. In accordance with a third non-limiting illustrative embodiment of the invention, the second non-limiting illustrative embodiment is modified so that the plane of the sensor electrodes forms an angle of approximately zero degrees with the vertical direction. In accordance with a fourth non-limiting illustrative embodiment of the present invention, the first, second and third non-limiting embodiments are further modified so that the sensor is fixed in the vat in a removable manner on a securing support.

In accordance with a fifth non-limiting illustrative embodiment of the present invention, the first, second, third and fourth non-limiting embodiments are further modified so that the sensor is directly fixed underneath the heating element of the cooking apparatus. In accordance with a sixth non-limiting illustrative embodiment of the present invention, the first, second, third, fourth and fifth non-limiting embodiments are further modified so that the sensor is secured on the securing part of the heating element, which extends parallel to the vertical walls of the vat.

BRIEF DESCRIPTION OF THE DRAWINGS

Other features and advantages of the present invention will appear more clearly in the following description of a preferred embodiment of a measuring device according to the invention, given by way of non-limiting example, with reference to the annexed drawings, in which.

DETAILED DESCRIPTION OF THE ILLUSTRATIVE EMBODIMENTS

Figure 1:
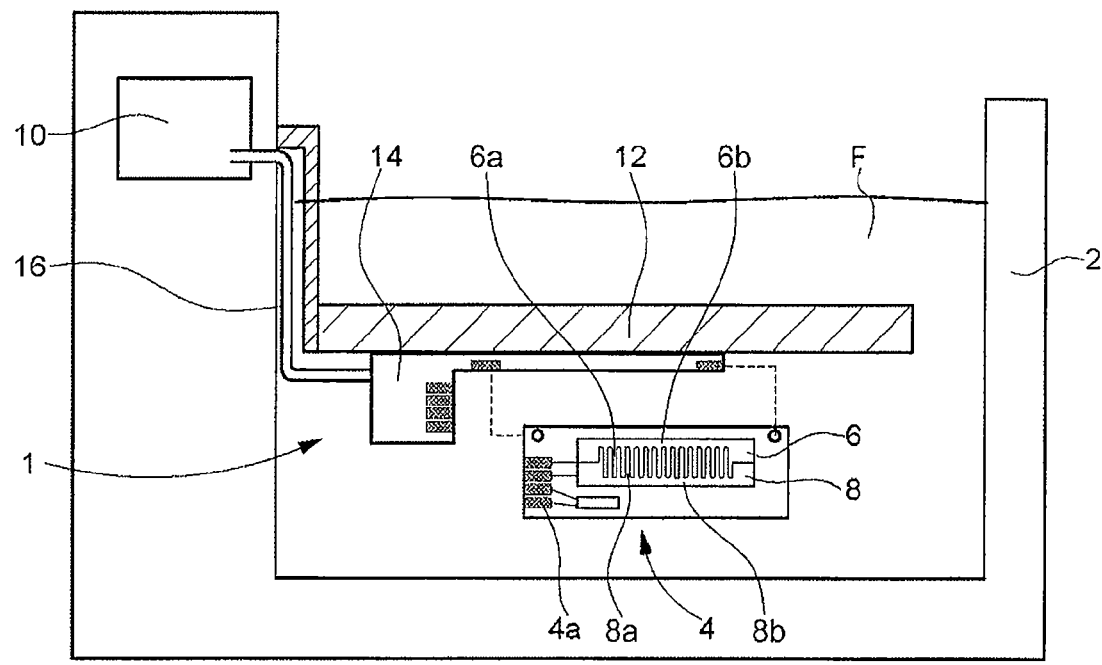
FIG. 1 is a schematic cross-section of the vat of a deep fat fryer, of a first embodiment of the measuring device with its encapsulated sensor according to the teaching of the invention.
Figure 2:
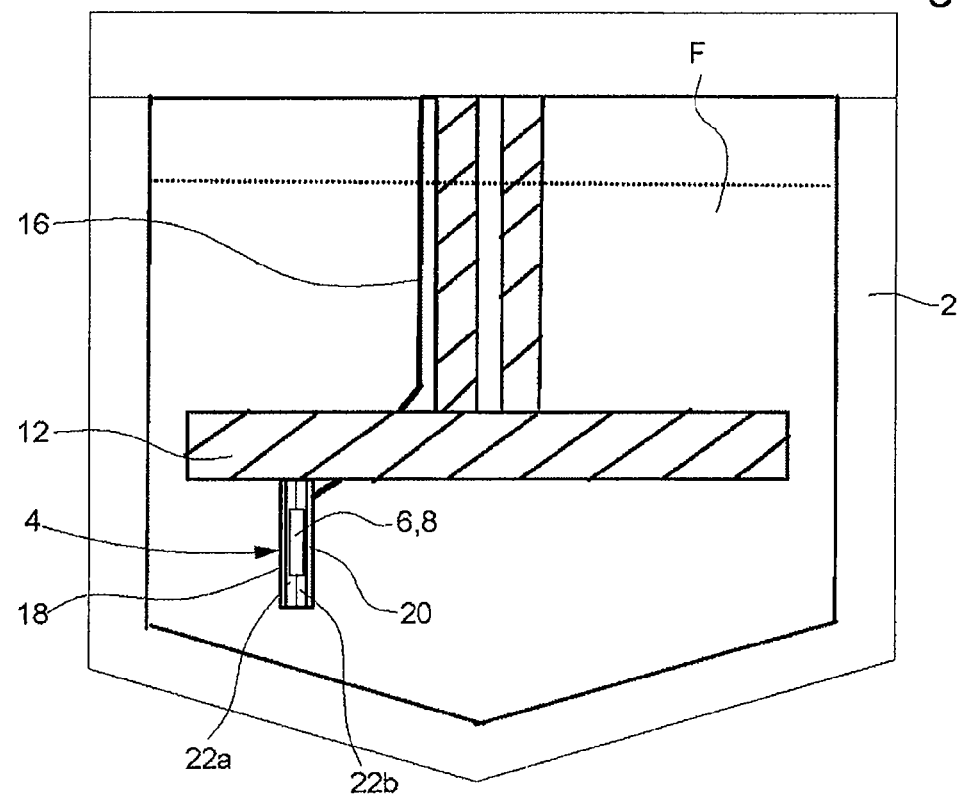
FIG. 2 is a schematic end view of the device shown in FIG. 1.

Referring to FIGS. 1 and 2, an embodiment of a device for the capacitive measurement of the quality and/or deterioration of a fluid, particularly an oil, is shown, designated by the general reference 1.

It will be noted that the following description will concern an application of a device 1 for measuring the quality and/or deterioration of an edible oil or similar, used for frying food in a cooking apparatus that has a vat 2 in which the oil can be heated, typically up to around 200° C.

Measuring device 1 has an encapsulated sensor 4 including a pair of electrodes 6, 8, which are spaced apart from each other and will be submerged in a fluid F (FIG. 2), for example the oil of a deep fat fryer, whose quality and/or deterioration one wishes to measure, in order to determine whether it is still fit for use. With oil F, electrodes 6, 8 form a capacitive measuring element EFM, whose capacitance varies as a function of the dielectric constant of the oil. When the oil deteriorates, the quantity of polar components present therein increases and causes an increase in the dielectric constant thereof. Thus, by measuring the evolution of the capacitance of capacitive measuring element EFM, one can determine the degree of quality and/or deterioration of the oil. Sensor 4, and more specifically its capacitive element EFM, is thus capable of providing an electrical output signal representative of the dielectric constant of the oil across a broad temperature range, in particular between 20° C. and 200° C. An electronic processing circuit 10, arranged outside vat 2, processes the electrical signal. Sensor 4 is connected to the electronic processing circuit by electric contacts 4a. The sensor is, for example, secured in a removable manner underneath heating element 12, via a securing and connecting support 14 integral therewith. Typically, sensor 4 can be plugged into support 14 via its electric contacts 4, which may, for example, take the form of elastic clamps. The securing and connecting support 14 is connected to the electronic circuit by means of cables 16 which are protected, for example in tubes.

Each electrode 6, 8 of the pair takes the form of a comb with a plurality of teeth 6a, 8a, which are approximately parallel to each other and extend from a base 6b, 8b. Electrodes 6, 8 are arranged in relation to each other such that the teeth 6a of one electrode 6 fit between the teeth 8a of the other electrode 8. The teeth of electrodes 6 and 8 are thus arranged in approximately the same plane.

It will be noted in this regard that electrodes 6 and 8 are, for example, formed from the same flat plate cut in a suitable manner, with the plate being sufficiently rigid for the electrodes to keep their shape when they are handled. In the example described, the electrodes are made from a plate of steel used for food (low carbon austenitic 18-10 stainless steel) with a thickness of between 0.1 and 3 mm. Other types of steel used for food may also be used, for example Z7CN18-09, Z3CND18-12-02, Z6CNDT17-12 and Z7CNU16-04. The plate is cut using a laser beam, which can make air gaps between the teeth of the electrodes of between 10 nm and 1 mm. It is clear that, the smaller the air gap, the greater the sensitivity of the capacitive element. According to a variant, one could also envisage making electrodes formed of a substrate coated with a conductive material, for example a substrate coated with a layer of gold, platinum or suchlike.

Electrodes 6 and 8 are arranged in a perforated encapsulating case. This case is formed of flat, perforated, metal plates 18, 29 between which electrodes 6 and 8 extend, with two pairs of spacers 22a, 22b and 24a, 24b made of insulating material inserted at the ends, between which electrodes 6, 8, which form the impedimetric sensor, are sandwiched. Electrodes 6, 8 are secured to plates 18, 20 via spacers 22a, 22b at one end and are guided freely between spacers 24a, 24b at their other end.

The perforations in plates 18, 20 of the encapsulating case are arranged opposite the measuring area of electrodes 6 and 8, i.e. opposite air gaps defined by the spaces between teeth 6a of electrode 6 and teeth 8a of electrode 8. Owing to this configuration, the fluid to be measured, in this case oil, bathes the other two faces of electrodes 6 and 8 on either side of the plane of the electrodes such that it can flow around teeth 6a and 8a of electrodes 6 and 8.

This electrode encapsulation structure optimises the flow of oil around the two faces of the flat electrodes and, in particular creates two channels C1, C2, respectively defined between a first surface of electrodes 6, 8 and the perforated plate 18 and a second surface of electrodes 6, 8, opposite the first surface, and perforated plate 20.

Electrodes 6 and 8 are secured to the spacers by elastic means, namely two strip springs 26, 28, which also fulfil the function of electric contact between the electrodes and contact elements 4a of sensor 2.

Mechanical uncoupling of the sensor from its encapsulating case is achieved via this elastic securing method. The strips, cut, via electro-erosion, into a stainless steel sheet that is 100 microns thick, position the sensor elastically in the encapsulating case. The sensor is guided in a perpendicular direction to the plane of plates 18 and 20 by securing elements 30a, 30b, which are housed in bores in spacers 24a, 24b. A small amount of play is left so that the sensor is "free" in its place, simply resting on the insulating parts.

The spacers are preferably made of a material that is resistant to temperatures of between 20"C and 200° C. and has a low thermal expansion coefficient, such as a ceramic material. However, they can be made of any other insulating material compatible with the application envisaged for the measuring device. By way of example, for a food-related application that has to be stable within the aforementioned temperature range, the spacers could also be made of a fluoride polymer such as Teflon.

The encapsulated sensor is oriented in the vat such that the longitudinal axis of each electrode base extends parallel to the bottom of the vat. The plane of the sensor electrodes forms an angle of approximately zero degrees with the vertical direction.

It is, however, clear that the plane of the sensor electrodes may also form an angle of between 0° and 60° with the vertical direction. The maximum angle is determined such that it allows a flow of oil around the impedimetric sensor, namely through channels C1 and C2 without impurities, mainly formed of breadcrumbs and bits of fried food, sticking to the surface of the sensor.

Figure 3:
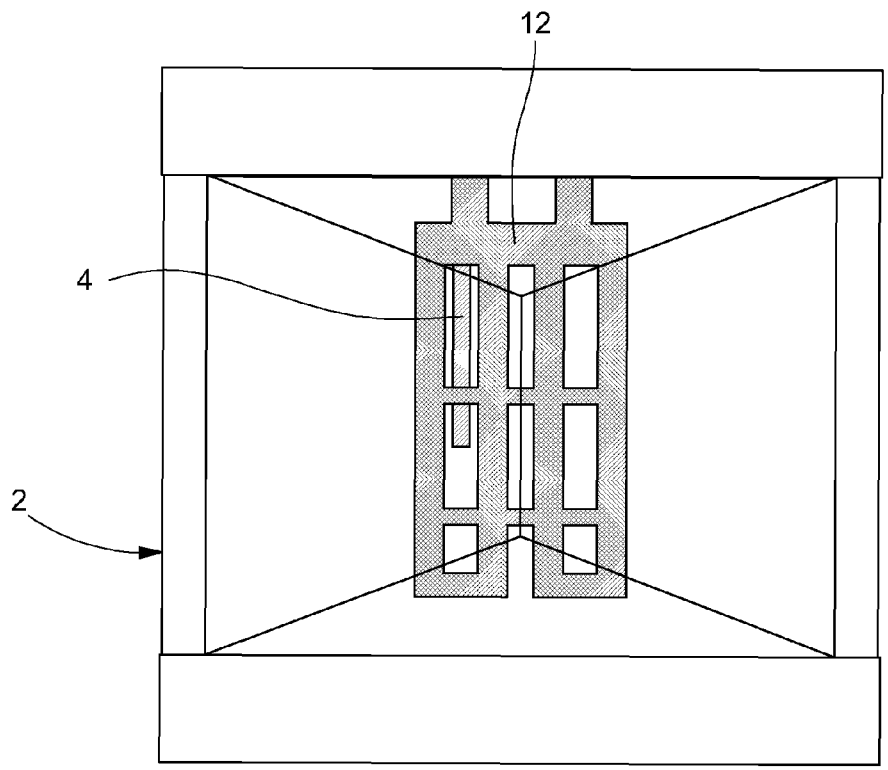
FIG. 3 is a schematic, top view of the device shown in FIG. 1.
Figure 4:
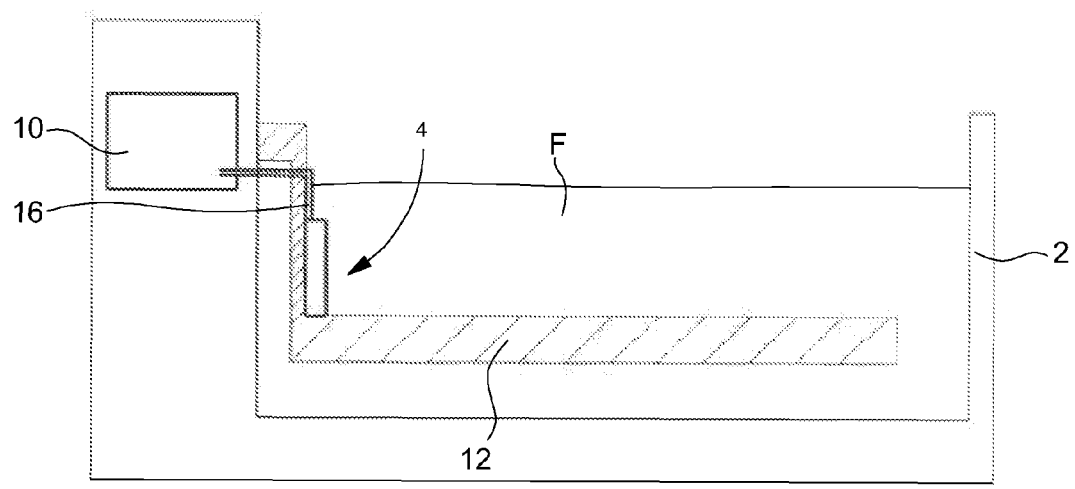
FIG. 4 is a schematic cross-section of the deep fat fryer vat of a second embodiment of the measuring device with the encapsulated sensor oriented in the vat in accordance with the teaching of the invention.
Figure 5:
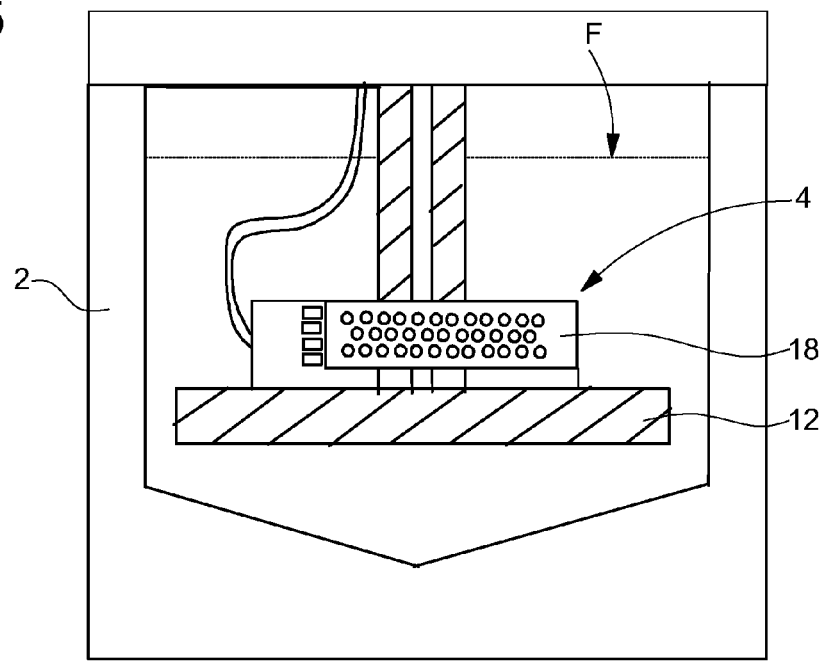
FIG. 5 is a schematic end view of the sensor shown in FIG. 4.
Figure 6:
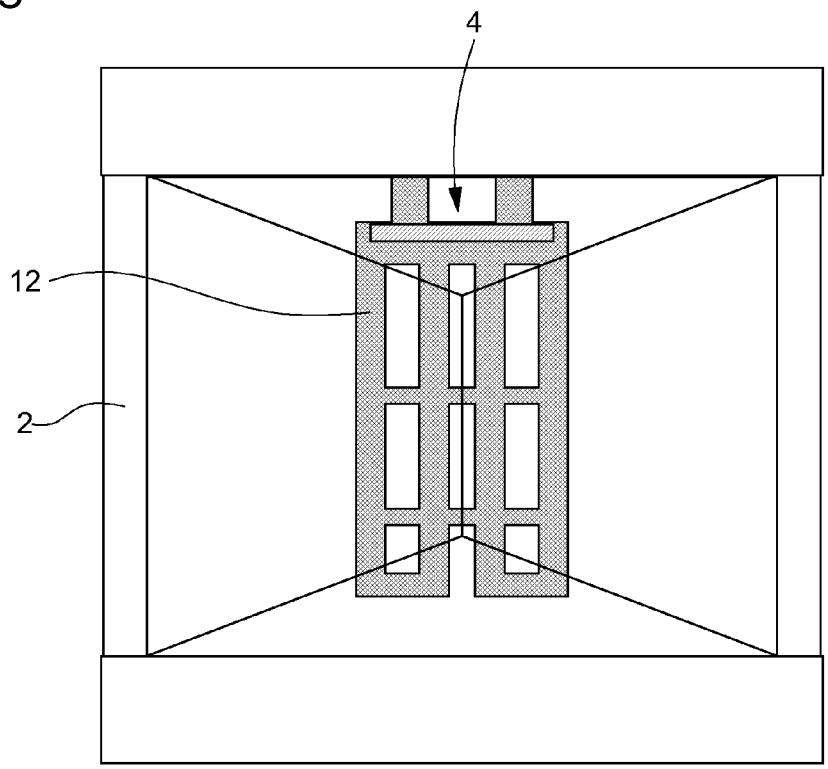
FIG. 6 is a schematic top view of the device shown in FIG. 4.
Figure 7:
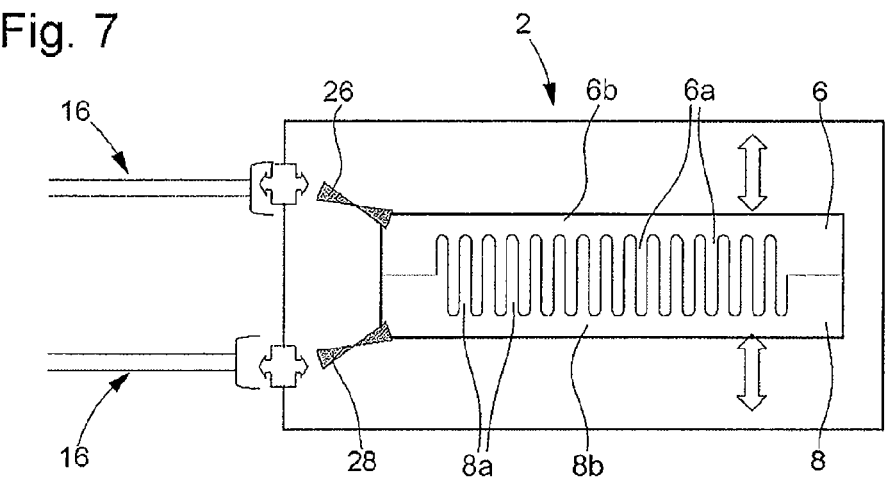
FIG. 7 is a schematic view of the encapsulated sensor of the device according to the invention.
Figure 8:
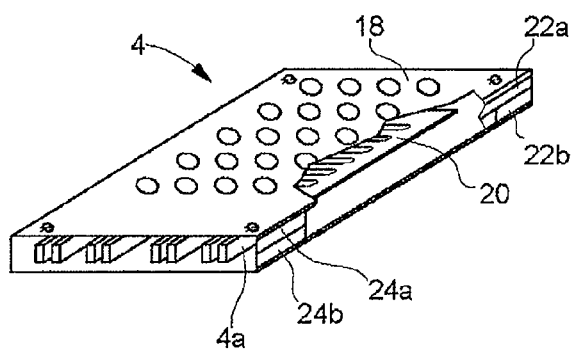
FIG. 8 is a schematic perspective view of the encapsulated sensor of the device according to the invention.
Figure 9:
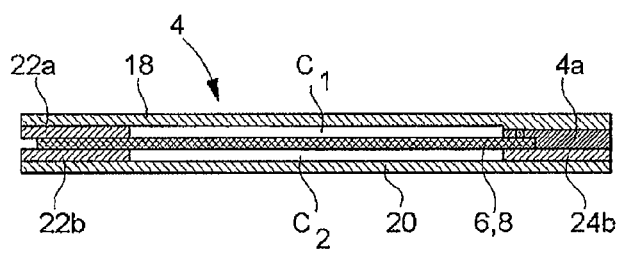
FIG. 9 is a schematic cross-section of the encapsulated sensor according to the invention.
Figure 10:
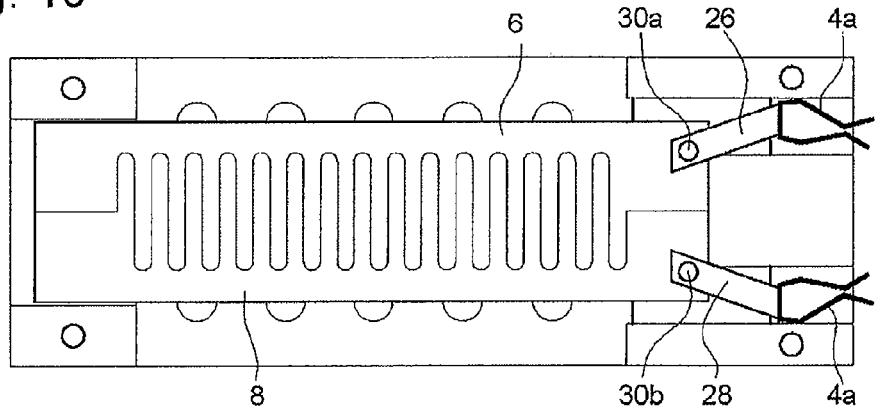
FIG. 10 is a schematic elevation of the unencapsulated sensor according to the invention.

According to the embodiment illustrated in FIGS. 1 to 3, the sensor is secured in the vat in a removable manner on a securing support, directly fixed underneath the heating element of the cooking apparatus of FIG. 1. According to the embodiment illustrated in FIGS. 4 to 6, the sensor is secured on a securing part of the heating element that extends parallel to the vertical walls of the vat.

However, while various modifications of the invention, and specific embodiments have been described above, when broadly construed, the invention concerns a device for the capacitive measurement of the quality and/or deterioration of a fluid, wherein the device includes a sensor encapsulated in a perforated case fixed in the vat of a cooking apparatus that has a bottom, wherein the sensor is connected to an electronic processing circuit, wherein the sensor includes a pair of flat electrodes that each have the shape of a comb with a plurality of teeth, which are approximately parallel to each other and extends from a base, which the electrodes are arranged in relation to each other such that the teeth of one electrode fit between the teeth of the other electrode in approximately the same plane, and wherein the encapsulated sensor is oriented in the vat such that the longitudinal axis of each electrode base extends parallel to the bottom of the vat and in that the plane of the sensor electrodes forms an angle of between 0° and 60° with the vertical direction.

The invention claimed is:

1. A device for capacitive measurement of the quality, or deterioration, or both the quality and deterioration, of a fluid, wherein the device is secured in a vat of a cooking apparatus, and the device includes:
   (a) a sensor encapsulated in a perforated case and secured in the vat of the cooking apparatus, wherein the vat includes a bottom; and
   (b) an electronic processing circuit, wherein the encapsulated sensor is connected to the electronic processing circuit, and wherein the sensor includes a pair of flat electrodes that each have a shape of a comb with a plurality of teeth that are arranged approximately parallel to each other and extend from a base, wherein the pair of flat electrodes include a first electrode and a second electrode that are arranged in relation to each other so teeth of the first electrode fit between teeth of the second electrode in approximately the same plane defining a first plane, and wherein the encapsulated sensor is oriented in the vat so a longitudinal axis of the base of each electrode extends parallel to the bottom of the vat and so the first plane of the first and second electrodes forms an angle of between 0° and 60° with a vertical direction extending parallel to vertical walls of the vat.

2. The device according to claim 1, wherein the first plane of the first and second electrodes forms an angle of between 0° and 30° with the vertical direction.

3. The device according to claim 2, wherein the first plane of the first and second electrodes forms an angle of approximately zero degrees with the vertical direction.

4. The device according to claim 1, wherein the encapsulated sensor is fixed in the vat in a removable manner on a securing support.

5. The device according to claim 1, wherein the encapsulated sensor is directly fixed underneath a heating element of the cooking apparatus.

6. The device according to claim 1, wherein the encapsulated sensor is secured on a securing part of a heating element that extends parallel to the vertical walls of the vat.

7. A device for capacitive measurement of the quality, or deterioration, or both the quality and deterioration, of a fluid, wherein the device is secured in a vat of a cooking apparatus, and the device includes:
   (a) a sensor encapsulated in a perforated case and secured in the vat of the cooking apparatus, wherein the vat includes a bottom; and
   (b) an electronic processing circuit, wherein the encapsulated sensor is connected to the electronic processing circuit, and wherein the sensor includes a pair of flat electrodes that each have a shape of a comb with a plurality of teeth that are arranged approximately parallel to each other and extend from a base, wherein the pair of flat electrodes include a first electrode and a second electrode that are arranged in relation to each other so teeth of the first electrode fit between teeth of the second electrode in approximately the same plane defining a first plane, and wherein the encapsulated sensor is oriented in the vat so a longitudinal axis of the base of each electrode extends parallel to the bottom of the vat and so the first plane of the first and second electrodes forms an angle of between 0° and 60° with a vertical direction.

8. A device for capacitive measurement of the quality, or deterioration, or both the quality and deterioration, of a fluid, wherein the device is secured in a vat of a cooking apparatus, and the device includes:
   (a) a sensor encapsulated in a perforated case and secured in the vat of the cooking apparatus, wherein the vat includes a bottom; and
   (b) an electronic processing circuit, wherein the encapsulated sensor is connected to the electronic processing circuit, and wherein the sensor includes a pair of flat electrodes that each have a shape of a comb with a plurality of teeth that are arranged approximately parallel to each other and extend from a base, wherein the pair of flat electrodes include a first electrode and a second electrode that are arranged in relation to each other so teeth of the first electrode fit between teeth of the second electrode in approximately the same plane defining a first plane, and wherein the encapsulated sensor is oriented in the vat so a longitudinal axis of the base of each electrode extends parallel to the bottom of the vat and so the first plane of the first and second electrodes forms an angle of zero degrees with a vertical direction.

* * * * *